(12) United States Patent
Yoshikawa

(10) Patent No.: US 9,131,923 B2
(45) Date of Patent: Sep. 15, 2015

(54) ULTRASONIC DIAGNOSTIC DEVICE AND ULTRASONIC IMAGE DISPLAY METHOD

(75) Inventor: Hideki Yoshikawa, Hino (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 218 days.

(21) Appl. No.: 13/810,524

(22) PCT Filed: Jul. 28, 2011

(86) PCT No.: PCT/JP2011/067200
§ 371 (c)(1),
(2), (4) Date: Jan. 16, 2013

(87) PCT Pub. No.: WO2012/029459
PCT Pub. Date: Mar. 8, 2012

(65) Prior Publication Data
US 2013/0116557 A1 May 9, 2013

(30) Foreign Application Priority Data
Aug. 31, 2010 (JP) .................... 2010-194253

(51) Int. Cl.
*A61B 8/00* (2006.01)
*A61B 8/08* (2006.01)
*A61B 8/06* (2006.01)
*A61B 8/14* (2006.01)

(52) U.S. Cl.
CPC .............. *A61B 8/5207* (2013.01); *A61B 8/06* (2013.01); *A61B 8/0891* (2013.01); *A61B 8/461* (2013.01); *A61B 8/463* (2013.01); *A61B 8/465* (2013.01); *A61B 8/481* (2013.01); *A61B 8/5223* (2013.01); *A61B 8/14* (2013.01)

(58) Field of Classification Search
CPC ......... A61B 8/06; A61B 8/481; A61B 8/5223
USPC .......................................... 600/458
See application file for complete search history.

(56) References Cited

U.S. PATENT DOCUMENTS

2005/0059893 A1  3/2005 Ogasawara et al.
2005/0187475 A1  8/2005 Nakaya
(Continued)

FOREIGN PATENT DOCUMENTS

CN    101721226       6/2010
EP    2 255 731 A1   12/2010
(Continued)

OTHER PUBLICATIONS

JP Office Action for Japanese Application No. 2012-531757, issued on Jan. 7, 2014.
(Continued)

*Primary Examiner* — Jonathan Cwern
(74) *Attorney, Agent, or Firm* — Baker Botts L.L.P.

(57) ABSTRACT

An ultrasonic diagnostic device and image display method display an inflow time map representing relative differences in blood flow dynamics such as inflow of a contrast agent, including extracting a vessel and constructing a noise-less inflow time map, and, in the comparison of differences in color between the constructed inflow time map and the past inflow time map, unifying the color of regions as a base. A TIC analysis unit calculates a parameter ($t_\alpha$) indicating an inflow starting time of a contrast agent and a difference of brightness $\Delta I$ due to the contrast agent using image data in a range designated by an image detection unit. A first pixel selection unit extracts a pixel and removes a non-contrast-enhanced region. An image construction unit constructs an inflow time map colored according to $t_\alpha$, and a second pixel selection unit extracts a vessel using a histogram based on $\Delta I$.

14 Claims, 12 Drawing Sheets

(56) References Cited

U.S. PATENT DOCUMENTS

| | | |
|---|---|---|
| 2009/0198123 A1 | 8/2009 | Aoyagi et al. |
| 2010/0094133 A1 | 4/2010 | Yoshiara et al. |
| 2010/0172562 A1 | 7/2010 | Satoh et al. |

FOREIGN PATENT DOCUMENTS

| | | |
|---|---|---|
| JP | 2001-269341 | 10/2001 |
| JP | 2005-81073 | 3/2005 |
| JP | 2005-185456 | 7/2005 |
| JP | 2009-183360 | 8/2009 |
| JP | 2010-5263 | 1/2010 |
| JP | 2010-94220 | 4/2010 |
| JP | 2010-158360 | 7/2010 |
| WO | WO 2009/110308 A1 | 9/2009 |

OTHER PUBLICATIONS

China Office Action for Chinese Application No. 201180036030.2, issued on May 4, 2014.

Bernard E. Van Beers Hepatic Perfusion Parameters in Chronic Liver disease: Dynamic CT Measurements Correlated with Disease Severity, American Roentgen Ray Society:176, Mar. 2001, pp. 667-673.

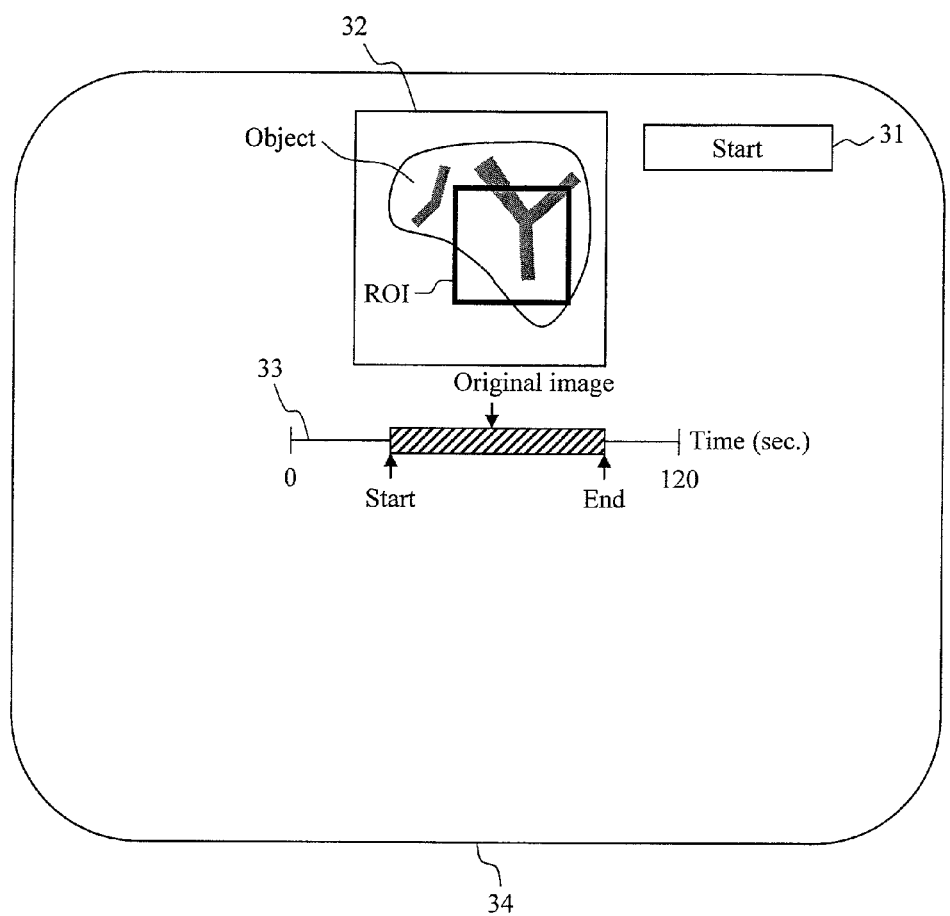

ULTRASONIC DIAGNOSTIC DEVICE AND ULTRASONIC IMAGE DISPLAY METHOD

TECHNICAL FIELD

The present invention relates to a technique of transmitting ultrasonic waves to the inside of a living body and of imaging information on the inside of the living body based on a signal received, and more particularly relates to an ultrasonic diagnostic device and an ultrasonic image display method of effectively detecting dynamic information on a blood flow based on a plurality of time-series contrast-enhanced images for imaging.

BACKGROUND ART

Ultrasonic diagnostic devices are one of common image display devices in clinical practice together with CTs and MRIs, and have features of compact in size and enabling motion picture imaging. Although the viewing field is limited, ultrasonic diagnostic devices have excellent spatial and time resolutions, and with the use of an ultrasonic contrast agent, micro-structured blood flow dynamics can be observed, and so the ultrasonic diagnostic devices have an important function to diagnose properties of tumors.

Although CTA (CT Angiography) has been a main-stream for observation means of blood flow dynamics, CTA has problems of exposure to radiation and toxicity of iodine contrast agents. Therefore the usage of CTA may be limited for patients suffering from kidney disease or having an allergy. Compared with this, ultrasonic contrast agents are microbubbles of a few μm in diameter and the agents themselves do not have any toxicity. Further since ultrasonic contrast agents have properties of resonating in a frequency bandwidth of medical ultrasonic waves to emit intense radiation of harmonic components, having a size equal to red blood cells to enter into small vessels, and being discharged from the body with the course of time mainly through exchange of gases in the lung, blood flow dynamics of small vessels can be observed easily.

Liver tumors are one of lesions that can be effectively observed with blood flow dynamics. It is known about liver tumors that blood vessels that are dominant at the lesion part shift from portal to asteriosity during the course of worsening from precancer states such as hepatitis and cirrhosis to liver cancer. It is known that as for liver tumors at an early stage, portal veins are dominant, through which blood via a digestive system flows, and as the clinical state progresses, dominant vessels shift to arteries (Non-Patent Literature 1).

Arteries and portal veins are different in inflow starting time and inflow-speed of a contrast agent due to their different circulatory pathways. Effective means to evaluate such a difference in blood flow dynamics is TIC (Time-Intensity Curve) that is obtained by plotting a change of brightness over time due to the inflow of a contrast agent. A contrast-enhanced image or the TIC of a lesion part enables early detection of the lesion or determination of its activity. Furthermore, since blood flow dynamics vary with types of lesions such as hepatocarcinoma, metastatic cancer and cyst, the contrast-enhanced ultrasonic techniques are regarded as important for effective imaging techniques in differential diagnosis of lesions.

The evaluation using blood flow dynamics is effective also to determine the effectiveness of cancer therapy. In the case of medical therapy using RF or medicines, blood flow dynamics in addition to the size of tumors are important targets of observation. This is because, even when a tumor does not change in size on the image, the effectiveness of the therapy can be determined based on dissipation of tumor vessels or a decrease in the amount of the blood flow Especially in the case of therapy such as an anti-angiogenic agent or vascular embolization therapy targeting at vessels serving as nutrient supply for tumors, the future therapeutic strategy will be decided by not only the presence or not of blood flow into a lesion but also whether the blood flow found is portal or asteriosity, and therefore blood flow dynamics are important targets of the observation to determine the effectiveness.

The technique described in Patent Literature 1 is to calculate statistic values such as average brightness values based on the measured TIC and display a color-coded image in accordance with the values. In this technique, firstly tissue is filled with a contrast agent under the irradiation of ultrasonic waves at a medium to low sound pressure level. Subsequently the contrast agent is cleaned out by irradiation of ultrasonic waves at a high sound pressure level, and a blood flow flowing back to the same imaging plane under irradiation of ultrasonic waves at a medium to low sound pressure level again is evaluated with TIC.

The technique described in Patent Literature 2 is to detect the inflow time of a contrast agent for each vessel and display relative differences therebetween in different colors. A region of interest is provided on a screen, and an image is colored while setting the inflow time in this region as a reference time.

CITATION LIST

Patent Literatures

Patent Literature 1: JP 2005-81073 A
Patent Literature 2: JP 2010-94220 A

Non-Patent Literature

Non-Patent Literature 1: Beers B. E. Vet al.: AJR 176, 667. 2001.

SUMMARY OF INVENTION

Technical Problem

It is an object of the invention to provide an ultrasonic diagnostic device and an ultrasonic image display method having a function of displaying an inflow time map representing relative differences in blood flow dynamics such as inflow time of a contrast agent in difference colors, including a function of selectively extracting a focused vessel and constructing a noise-less inflow time map, and in the comparison of differences in color between the constructed inflow time map and the past inflow time map to examine a change in blood flow dynamics by therapy or the like, an interpolation function of unifying the color of regions as a base.

Solution to Problem

In the present invention, a TIC analysis unit 13 calculates a parameter ($t_α$) indicating an inflow starting time of a contrast agent and a difference of brightness $\Delta I$ due to the contrast agent using image data in a range designated by an image detection unit 11. A first pixel selection unit 15 selectively extracts a pixel meeting certain conditions and concurrently removes a non contrast-enhanced region. An image construction unit 16 constructs an inflow time map colored in accordance with the values of $t_α$, and a second pixel selection unit 17 selectively extracts a vessel focused by an operator using a histogram based on the difference of brightness.

Advantageous Effects of Invention

According to the present invention, a focused vessel can be selectively extracted, and an inflow time map with good viewability can be presented.

BRIEF DESCRIPTION OF DRAWINGS

FIG. 3 describes a step of selecting an image to be processed in one embodiment.

DESCRIPTION OF EMBODIMENTS

Figure 1:
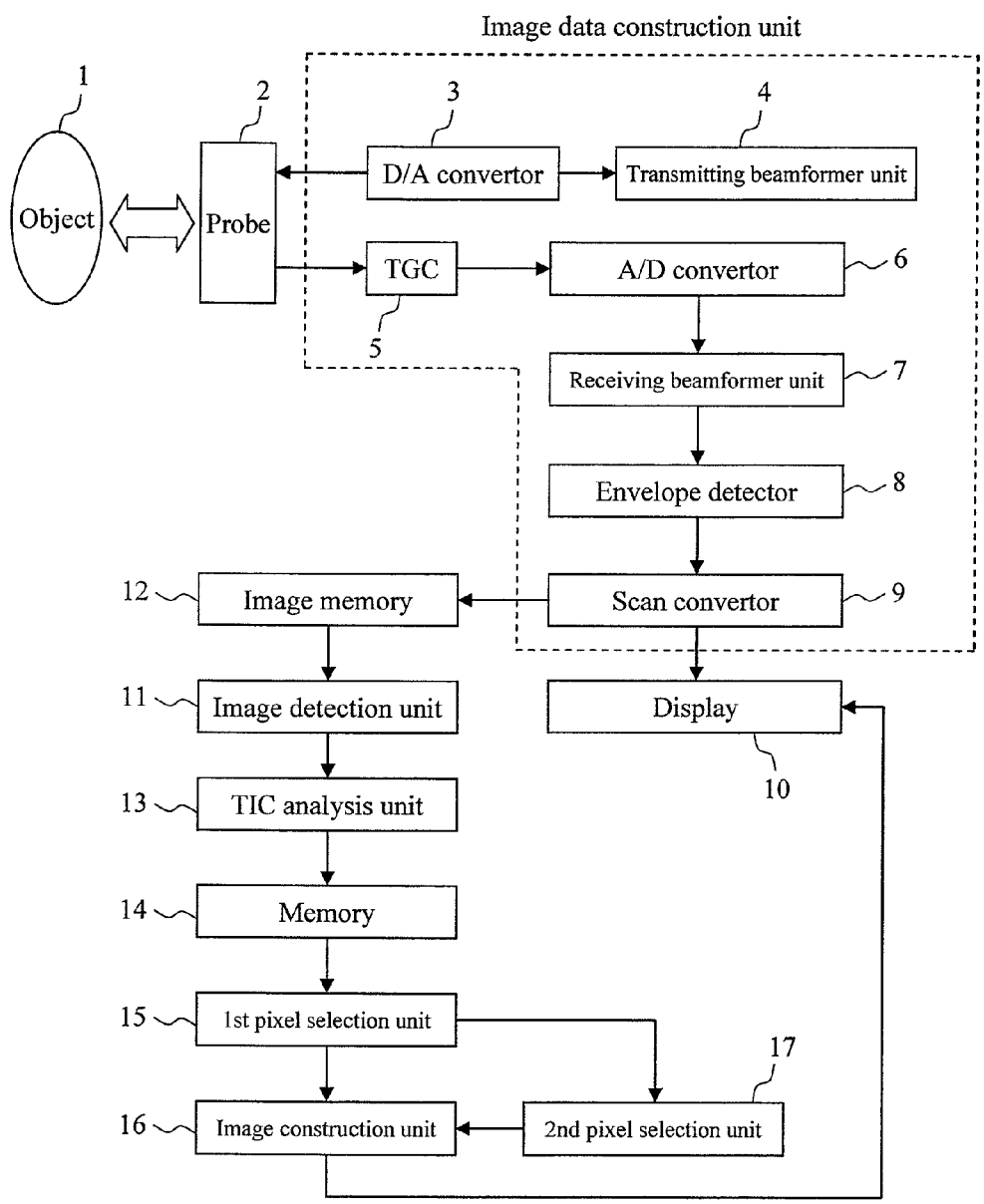
FIG. 1 is a block diagram illustrating an exemplary configuration of one embodiment.

The following describes embodiments of the present invention, with reference to the drawings. FIG. 1 is a block diagram of an ultrasonic diagnostic device as an embodiment. The ultrasonic diagnostic device as the embodiment includes: a probe 2 that transmits and receives ultrasonic signals to and from an object 1; a transmitting beamformer unit 4 and a receiving beamformer unit 7 that provide a predetermined time delay to a piezoelectric element making up the probe 2 to form a desired transmitting/receiving beam; an A/D convertor 6 and a D/A convertor 3 for analogue/digital conversion of transmitted/received signals; a TGC (Time Gain Controller) 5 that compensates for amplitude attenuation generated during the propagation of ultrasonic signals inside a living body; an envelope detector 8 that detects a received RF signal and converts the signal into an image signal; and a scan convertor 9 that constructs two-dimensional image data from the image signal. These elements configure a generally known image data construction unit to construct an ultrasonic image. The present embodiment further includes: an image memory 12 that stores image data from the scan convertor 9; an image detection unit 11 that selects a data range to be used to construct an inflow time map from the storage image data, by receiving information containing a starting time when a contrast agent is given to a test object, for example; a TIC analysis unit 13 that finds parameters necessary to evaluate blood flow dynamics from the selected image data; a memory 14 that stores numeric values calculated by the TIC analysis unit 13; a first pixel selection unit 15 that extracts and removes a pixel in accordance with conditional expressions set in the device beforehand; an image construction unit 16 that constructs an inflow time map using the numeric values stored in the memory 14; and a second pixel selection unit 17 that extracts a pixel again from the image constructed by the image construction unit 16 using brightness information and time information, thus extracting information focused by an operator.

Image data constructed by the image data construction unit refers to a monochrome image (B mode) or an image using a contrast agent (an image where signals from a contrast agent are emphasized using a transmission/reception sequence, filter processing or the like) that is generally used in clinical practice. Since a method for constructing such an image is generally known, just a brief explanation is given here. The probe 2 has an ultrasonic emission surface configured as a one-dimensional array where a plurality of piezoelectric elements are aligned in one line, each element having a function of transmission/reception of ultrasonic waves. A voltage pulse from the transmitting beamformer unit 4 is input to each piezoelectric element via the D/A convertor 3, and piezoelectric vibrations of the elements cause irradiation of ultrasonic waves toward the object 1. At this time, a predetermined time delay is electronically given to each piezoelectric element, and the ultrasonic waves transmitted from these piezoelectric elements come into a focus at a predetermined position inside the object 1. Reflection echo from the object 1 is received by each piezoelectric element, and is subjected to amplitude compensation by the TGC 5 depending on the propagation distance. Subsequently, the received signal is sent to the receiving beamformer unit 7 via the A/D convertor 6, to which a delay time depending on the distance from the focus position to each piezoelectric element is applied, and a result of addition is output (phasing and adding).

Exemplary well-known techniques to enhance a signal from a contrast agent for imaging include a technique of transmitting two signal having phases inverted to each other and adding received signals thereof The addition of the received signals can suppress fundamental frequency components mainly associated with tissue components, while emphasizing harmonic components mainly associated with signals from the contrast agent. As a result, a contrast-agent emphasized image can be obtained.

Ultrasonic waves are transmitted and received by all scanning lines along with the line of the piezoelectric elements, whereby a two-dimensional distribution of reflection echo of the object 1 can be obtained. The receiving beamformer unit 7 outputs an RF signal including a real part and an imaginary part that are separated, and the RF signal output is sent to the envelope detector 8. The signal sent to the envelope detector 8 is converted into a video signal, to which pixel interpolation between scanning lines is applied at the scan convertor 9 for reconstruction into two-dimensional image data, and such data is displayed on a display 10.

Figure 2:
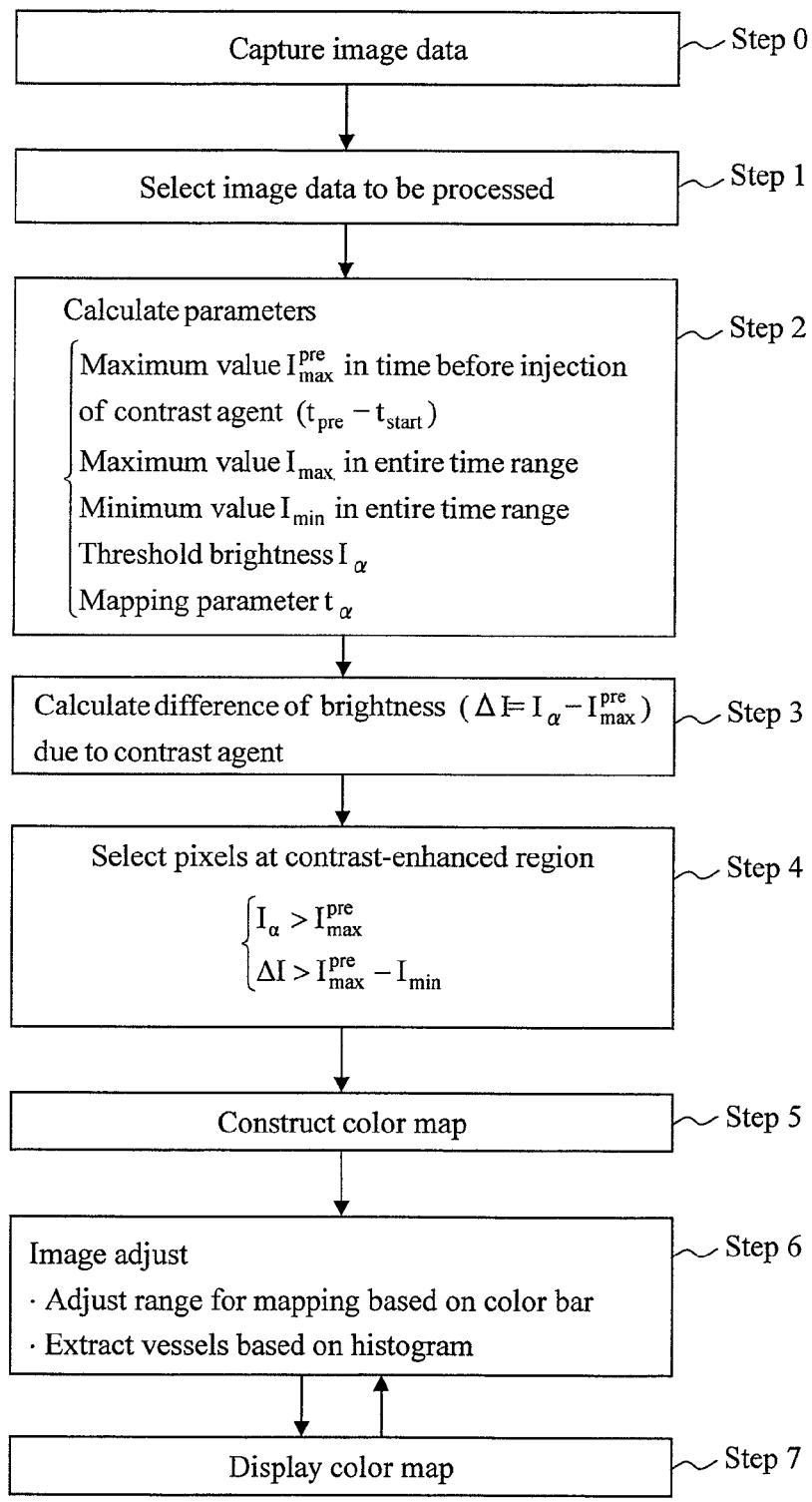
FIG. 2 describes processing steps of one embodiment.

Referring to the flowchart of FIG. 2, the following describes a method for displaying an ultrasonic image to construct an inflow time map using image data from the scan convertor 9.

Firstly, an operator fixes the probe 2 in a state where the probe captures the object 1 in an imaging plane, and administers a contrast agent. Concurrently with the administration of the contrast agent or before and after the administration, the operate presses a start button on the device to capture image data, thus storing time-series image data from the stage when the contrast agent flows into the object to the stage the target is filled with the contrast agent in the image memory 12 (Step 0). Next, image data to be used for evaluation of blood flow dynamics is selected from the captured image data (Step 1).

Selecting a set of image data to be used from the image memory 12 leads to, as shown in FIG. 3, display of selected image data 32, a start button 31 to indicate start of processing of an inflow time map and a time range bar 33 to indicate a time range of the image data. The units of the time range bar 33 may be seconds setting the initial value as 0 second or may be frame numbers setting the initial value at 1. The time range bar 33 is provided with an arrow indicating a time position of the current image, and image data at a time position designated by the operator can be displayed sequentially. The time range bar 33 is further provided with a start arrow and an end arrow to designate the range of image data to be processed, and so the operator designates the start and end range of image data to be used for inflow time map processing while observing the image data (Step 1). In this occasion, in order to mainly observe blood flow dynamics, the start arrow is typically set at a time immediately before or immediately after the inflow of a contrast agent to the object 1. It is appropriate to set the end arrow at a position where the inflow of the contrast agent into the focused vessel is finished or when a contrast-enhanced imaging of a tissue can be confirmed through angiography. In the former case, useful information for judgment as to whether arteries or portal veins are dominant at the lesion part can be obtained. In the latter case, the injection procedure of the contrast agent can be observed at not only vessels but also from vessels to a tissue region based on differences in color, and therefore useful information to identify a lesion or identify a major feeding vessel for the lesion can be obtained. Especially in the occasion for therapy targeting at vessels, it is very useful for identification of a target or judgment of effects from the therapy, but the processing time is accordingly increased.

Some ultrasonic diagnostic devices have a function of temporarily cleaning out a expanded contrast agent in the imaging plane of the object using high sound-pressure ultrasonic waves, and using this function, the contrast agent flowing into the imaging plane again may be observed after the irradiation of the high sound-pressure ultrasonic waves. In that case, image data corresponding to the time for the high sound-pressure irradiation can be easily specified based on the integral value or the average value of the brightness of image data, for example, and the start arrow may be automatically placed at the position of this image data.

A ROI on the image data may be used for spatial range designation, whereby processing cost can be reduced.

After designation of the range of image data, selecting the start button 31 leads to automatic resetting of a time one second ahead of the starting time designated at Step 2 as a new starting time, and image data in this range is sent to the TIC analysis unit 13. Image data for 1 second immediately before the starting time designated by the operator is used to calculate difference of brightness due to a factor other then the contrast agent. The numeric value of 1 second is set beforehand as a time corresponding to one heartbeat, and brightness fluctuations during this period can be regarded as the fluctuations of a speckle pattern mainly generated by heartbeats. The calculated difference of brightness is always inherent in TIC, which is a value necessary to precisely calculate the difference of brightness due to a contrast agent from the TIC. The setting of 1 second can be freely changed by the operator, and can be adjusted appropriately in accordance with heartbeats of a patient, for example. When the newly set starting time exceeds the range of the image data obtained, 0 second is set as the starting time.

Figure 4A:
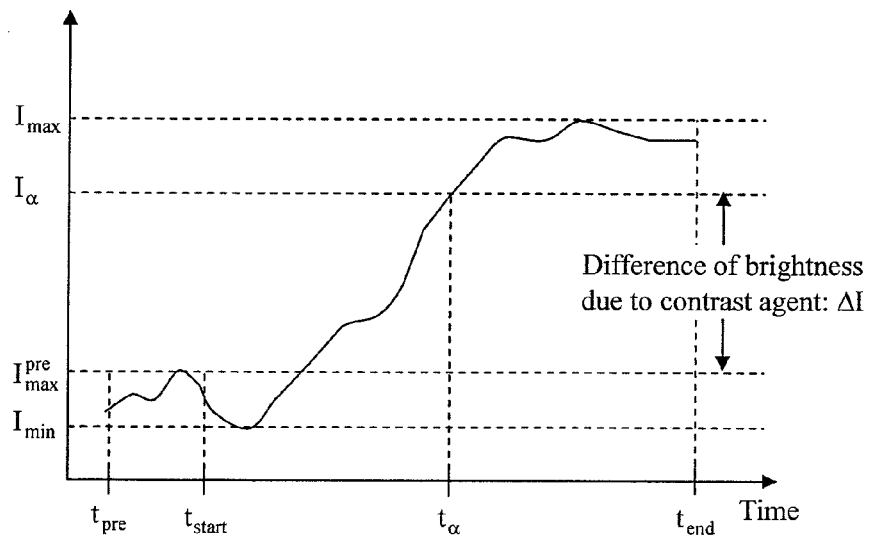
FIG. 4A describes a relation between TIC and measurement values in one embodiment.
Figure 4B:
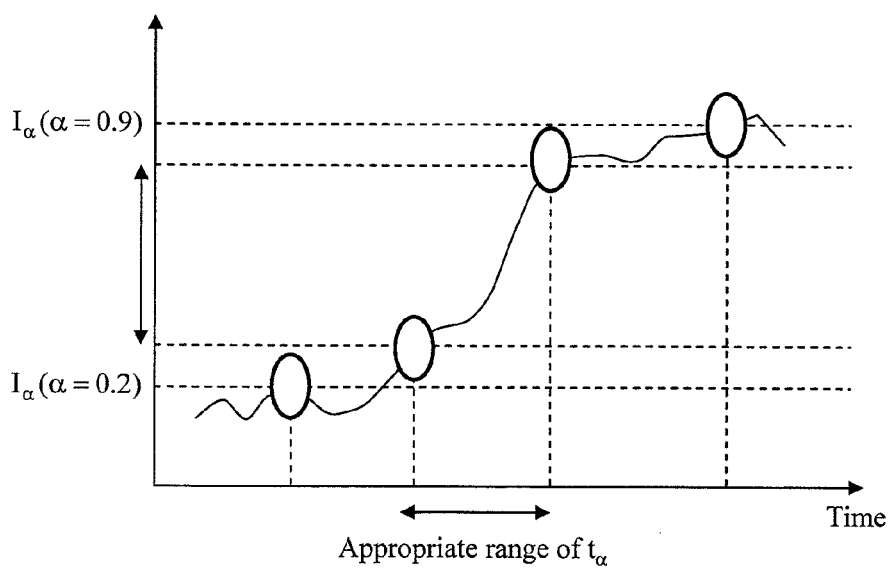
FIG. 4B describes a coefficient for a threshold brightness in one embodiment.

The TIC analysis unit 13 calculates, from a TIC, a maximum value $I^{pre}_{max}$ in the time range ($t_{pre}$-$t_{start}$) before injection of contrast agent, a maximum value $I_{max}$ and a minimum value $I_{min}$ in the entire processing range ($t_{start}$-$t_{end}$), threshold brightness $I_\alpha$ set by the operator beforehand and a time $t_\alpha$ when reaching the threshold brightness for each pixel (Step 2). FIG. 4A shows relations between parameters calculated by the TIC analysis unit 13 and the TIC. As described above, $t_{pre}$ is a value of 1 second ahead of the starting time that the operator sets at Step 1. The following describes, as an evaluation value (a mapping parameter) to construct an inflow time map, $t_\alpha$ indicating an inflow starting time of the contrast agent. Actually, however, various statistic values found from the TIC such as a maximum value and an average value that can be measured from the TIC can be candidates for the mapping parameter, among which an operator can select a value freely. $I_\alpha$ is a value obtained by multiplying the maximum value $I_{max}$ by coefficient $\alpha$ that the operator sets beforehand. The value of the coefficient $\alpha$ can be decided freely by the operator, and when the inflow starting time of the contrast agent is set as the mapping parameter, an appropriate value for $\alpha$ may be about 0.5 to 0.8 empirically. In order to calculate appropriate $t_\alpha$, as shown in FIG. 4B, the "inclination" of the TIC, i.e., the peak of inflowing contrast agent has to be captured as the threshold brightness. In the drawing, as examples of inappropriate $\alpha$, $\alpha=0.9$ and $\alpha=0.2$ are shown. It can be understood that in both of the case, the TIC reaches the threshold brightness at a position not relating to the inflow of the contrast agent, resulting in the calculation of inappropriate $t_\alpha$. The following describes the case of $\alpha=0.8$.

When the TIC analysis unit 13 calculates a parameter, it is desirable to perform averaging about 3 to 5 frames of the TIC. This processing can remove the influences of electrical noise included in the image data from the TIC, thus enabling calculation of a more precise parameter. At this time, the frequency of sampling of image data (the number of pieces of image data per unit time) is preferably maintained.

Next, based on the parameter calculated by the TIC measurement unit 13, a difference of brightness $\Delta I$ ($=I_\alpha - I^{pre}_{max}$) is calculated for each pixel (Step 3). Factors of fluctuations of TIC include the inflow of a contrast agent and movement of a tissue. When the probe is fixed and breathing is controlled by holding breath, for example, presumably the brightness fluctuations due to the movement of a tissue mainly result from fluctuations of speckle due to heartbeats. Accordingly, $\Delta I$ obtained by subtracting the maximum value $I^{pre}_{max}$ of the brightness fluctuations at the stage before injection of a contrast agent from $I_\alpha$ is calculated as the difference of brightness. Further, the magnitude of the value of $\Delta I$ reflects the amount of blood flow, which becomes an effective index to judge the types of vessels such as arteries, portal veins and tumor vessels. The numeric values calculated by the TIC analysis unit 13 and $\Delta I$ are stored in the memory 14.

Next, the first pixel selection unit 15 selectively extracts a pixel at a contrast-enhanced region (Step 4). The selected pixel meets the following two conditions.

$I_\alpha > I^{pre}_{max}$; and  Condition 1:

$\Delta I > I^{pre}_{max} - I_{min}$.  Condition 2:

The first pixel selection unit 15 leaves a pixel that might be a contrast-enhanced region, and removes a pixel that can be certainly determined as a non contrast-enhanced region or a pixel that would become noise of an inflow time map certainly. Condition 1 means that the threshold brightness exceeds the maximum brightness of the stage before injection of contrast agent. Since a pixel not meeting this condition will show the same brightness fluctuations as those at the stage before injection of contrast agent even at the contrast-agent injection stage, such a pixel is determined as a non contrast-enhanced region where the inflow of contrast agent is not found. Conversely when this pixel is determined as a contrast-enhanced region, an incorrect mapping parameter is more likely to be calculated as shown in FIG. 4B. Condition 2 means that the difference of brightness ($I^{pre}_{max}-I_{min}$) due to heartbeats and body movement is smaller than the difference of brightness ($\Delta I$) due to the contrast agent. When Condition 1 does not hold, $\Delta I$ will be negative and so Condition 2 will not hold. The following describes a pixel that meets Condition 1 but does not meet Condition 2. Image data used in the present embodiment basically is an image where a signal from a contrast agent is emphasized and a signal from a tissue is suppressed. In addition to that, a pixel not meeting Condition 2 is a pixel that does not have a contrast-enhanced effect or hardly has the effect. Since the pixel meets Condition 1, the TIC of this pixel increases at the stage of contrast-agent injection, but the factor thereof can be considered as entering of a tissue component due to body movement or the like and not the contrast agent, and therefore such a pixel is determined as a non contrast-enhanced region.

A pixel that does not meet the above Conditions 1 and 2 is considered as a non contrast-enhanced region, and the mapping parameter $t_\alpha$ and $\Delta I$ are made 0. The first pixel selection unit 15 has a relatively small effect of removing a non contrast-enhanced region. The first pixel selection unit 15 removes a pixel that can be certainly considered as a non contrast-enhanced region, and a pixel where determination between a contrast-enhanced region and a non contrast-enhanced region includes ambiguity is extracted if possible so as not to lose necessary information. A focused vessel is mainly extracted at a later stage by the second pixel selection unit 17, and the first pixel selection unit 15 acts in an auxiliary manner therefor. This mechanism can improve the viewability of the initial image of an inflow time map, and image adjustment by the operator at Step 6 as a second pixel selection processing can be facilitated. On the other hand, without the function of the first pixel selection unit 15, the color distribution of the initial image will be in disorder because of a random number of $t_\alpha$ that a pixel of a non contrast-enhanced region has. Especially the viewability of small vessels is degraded, and image adjustment by the second pixel selection unit 17 becomes difficult, and additionally a vessel to be focused may be overlooked.

Figure 5:
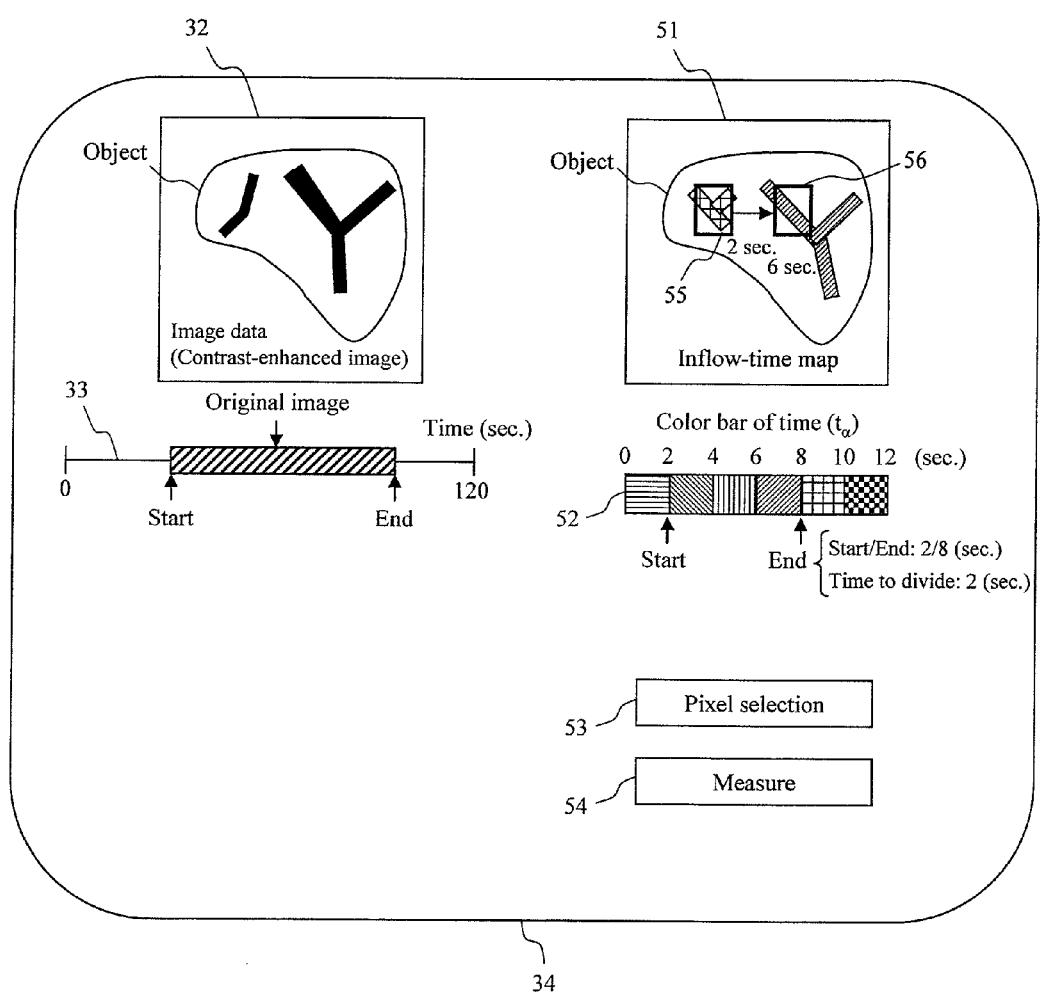
FIG. 5 describes pixel extraction using a color bar of time in one embodiment.
Figure 9:
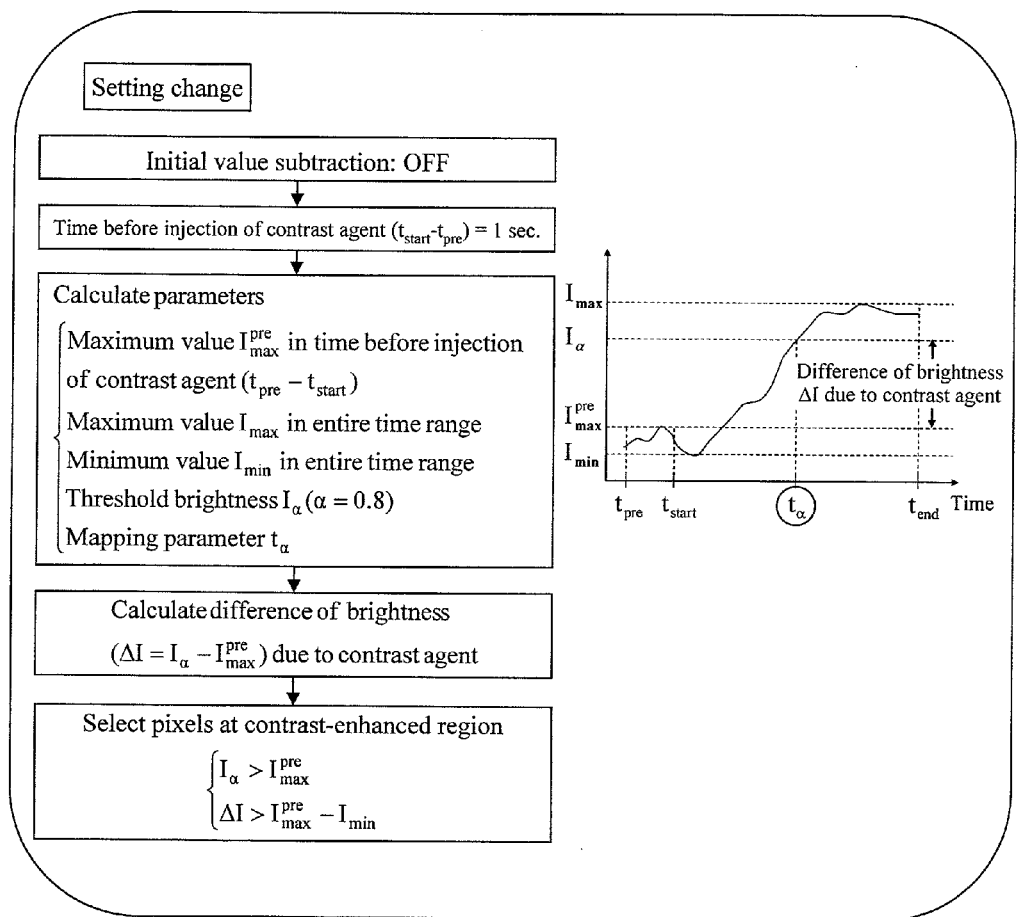
FIG. 9 describes setting change in one embodiment.

Subsequently at Step 5, as shown in FIG. 5, an inflow time map 51 color-coded in different colors in accordance with the values of the mapping parameter $t_\alpha$ found for the pixels is displayed on a display screen 34 together with the image data 32. The value $t_\alpha$ in this case is a time when the brightness reaches the value $I_\alpha$ obtained by, as stated above, multiplying the maximum value $I_{max}$ by the coefficient a set beforehand. The reason for using $t_\alpha$ is because relative values corresponding to the pixels for the starting time of a contrast agent at a focused portion can be compared. Although the original contrast agent starting time is $t_{start}$, as illustrated in FIG. 9, there are a plurality of times having the same brightness value, and so it is difficult to decide when is the starting time as $t_{start}$. On the other hand, the calculated $t_\alpha$ can be considered as one point at any pixel, thus enabling the comparison.

Referring back to FIG. 5, a pixel with $t_\alpha=0$ is not colored. Based on the color distribution of an inflow time map displayed, the inflow starting time of the contrast agent at a focused tissue can be compared relatively. As a result, the property of a dominant vessel at a target lesion can be found, such as portal or asteriosity, from which useful information for differential diagnosis can be obtained.

Figure 6:
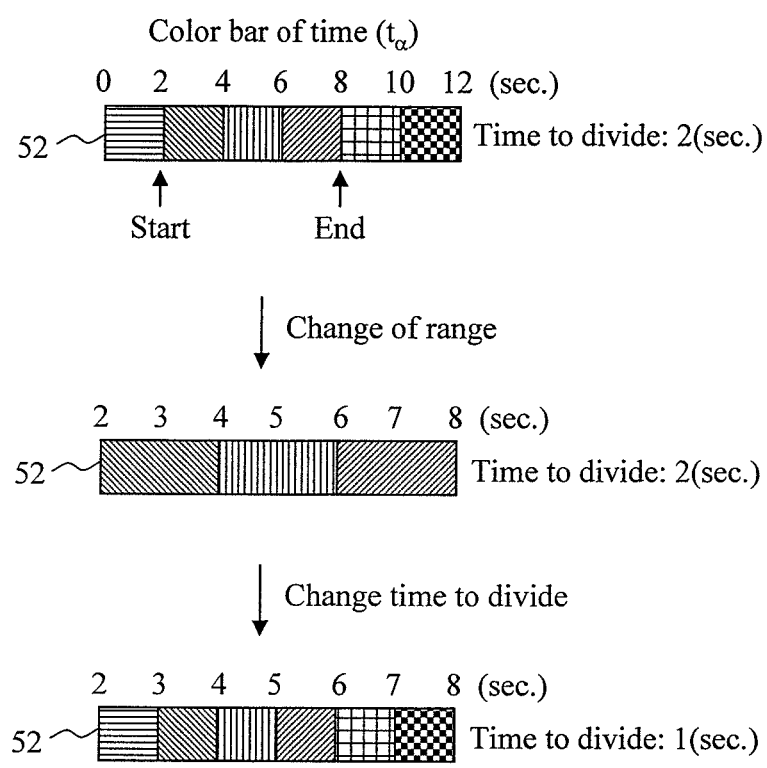
FIG. 6 describes a change in range of a color bar of time in one embodiment.

At Step 6, mapping information such as a range for mapping of an inflow time map, color-coding and vessel extraction is adjusted. The inflow time map 51 is provided with a color bar of time 52 indicating a corresponding relation between numeric values of time of the mapping parameter and colors, and the color bar of time is represented with a relative time while setting the starting time $t_{pre}$ of the processing as 0. When the positions of the starting point and the ending point provided in the color bar of time 52 are changed, as shown in FIG. 6, the minimum value and the maximum value of the color bar of time 52 are changed to the starting point and the ending point. At the same time, the correspondence between time and colors is changed as well. The changed result is reflected in the color-coding of the corresponding each pixel, thus updating the inflow time map 51. The value of $t_\alpha$ of a pixel beyond the setting range is made 0, and the color thereof is removed from the inflow time map. Further as shown in FIG. 6, a change of time to divide can change the division of the color-coded time, and such a change also can be reflected in the inflow time map as needed. The starting point and the ending point can be set by directly changing the numeric values displayed on the display screen 34.

Selecting a measure 54 button provided on the display screen 34 leads to display of a first ROI 55 on the inflow time map 51, where an absolute inflow time with reference to the starting point is displayed in a numeric value. Selecting the measure button again leads to display of a second ROI 56. In the second ROI 56, a relative difference in inflow time from the first ROI 55 is displayed in a numeric value. In order to indicate a relative relation, an arrow is drawn from the first ROI 55 to the second ROI 56. Selecting the arrow in the screen leads to display of an absolute difference in flowing time with reference to the starting point for the second ROI 56 as well, and the arrow disappears. This measurement function enables quantitative evaluation on a relative difference in blood flow dynamics between two vessels.

As stated above, the time range and the color-coding of the inflow time map are adjusted freely, whereby a vessel in the time range focused by the operator can be extracted precisely, and an image can be adjusted to be in an easy observation form for displaying.

A change of the time range enables selection of the range focused by the operator and adjustment of the color-coding. Therefore, at this stage, a noise component remains on the inflow time map, mainly including the pixels of the non contrast-enhanced region that cannot be removed at Step 4, and especially in the case of a relatively thin vessel such as a tumor vessel, the vessel may be buried in the noise. Since a contrast-enhanced region and a non contrast-enhanced region are differentiated effectively by using not time information but brightness information, the differentiation is performed by an image adjustment function based on $\Delta I$.

Figure 7:
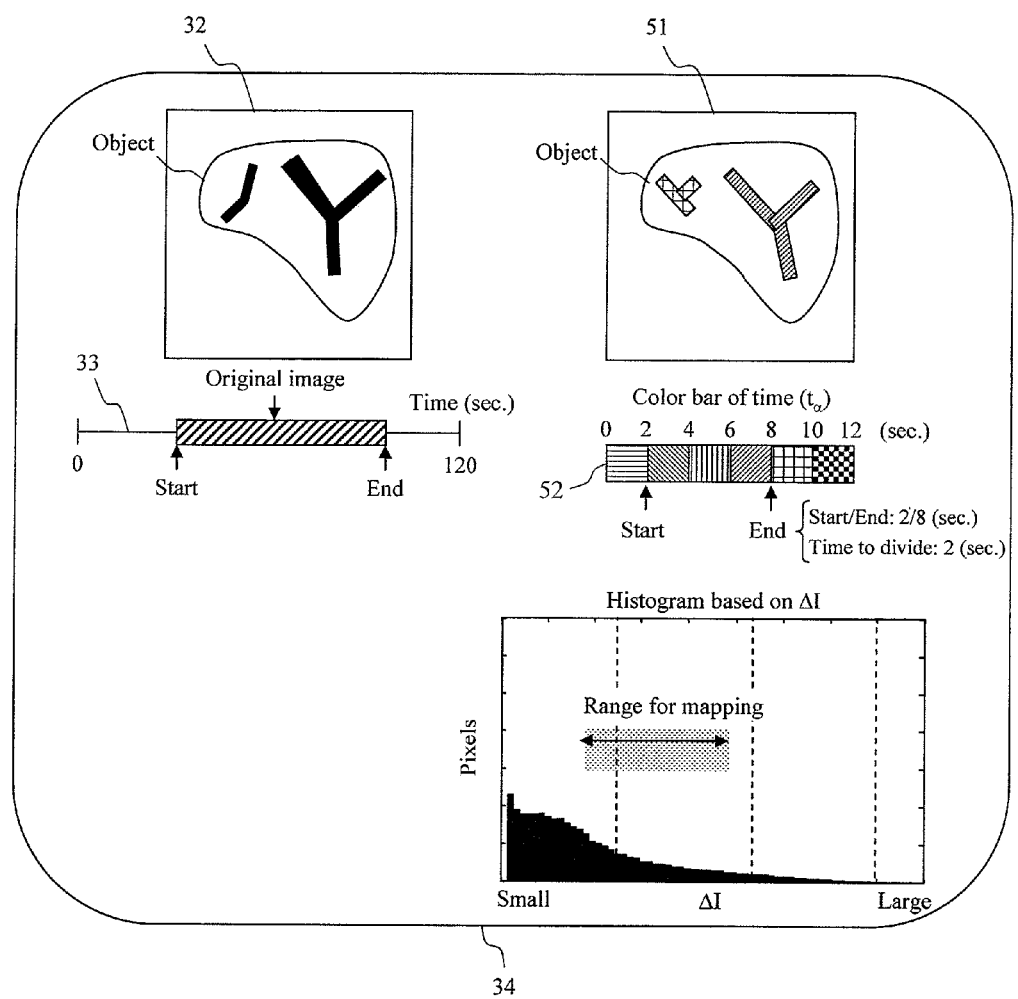
FIG. 7 describes pixel extraction using a histogram in one embodiment.

As shown in FIG. 5, when the operator presses a pixel selection 53 button provided on the display screen, the second pixel selection unit and the image construction unit operate to display a histogram as shown in FIG. 7, the histogram having the horizontal axis representing $\Delta I$ and the vertical axis representing the number of pixels. The histogram does not include $\Delta I=0$. Pixels not meeting the conditions at the first pixel selection unit are made 0, and the number of pixels here is more likely to be a very larger value than the number of pixels of other values. Further this value is not necessary to adjust the inflow time map, the range of $\Delta I>0$ is displayed so as to improve the viewability of the histogram. On the histogram, an arrow or a color-coded region indicating the range for mapping or both of them are displayed. When the operator designates the range for mapping of $\Delta I$ on the histogram, then the second pixel selection unit instantly makes the mapping parameter of the pixels having ΔI beyond the range 0, and removes the color from the inflow time map. Since ΔI of the pixels corresponding to the non contrast-enhanced region is much smaller than that at the contrast-enhanced region, removal of this range from the range for mapping enables effective removal of noise.

Since a thicker vessel tends to have a larger ΔI, selective extraction depending on the vessel size is enabled.

Figure 8:
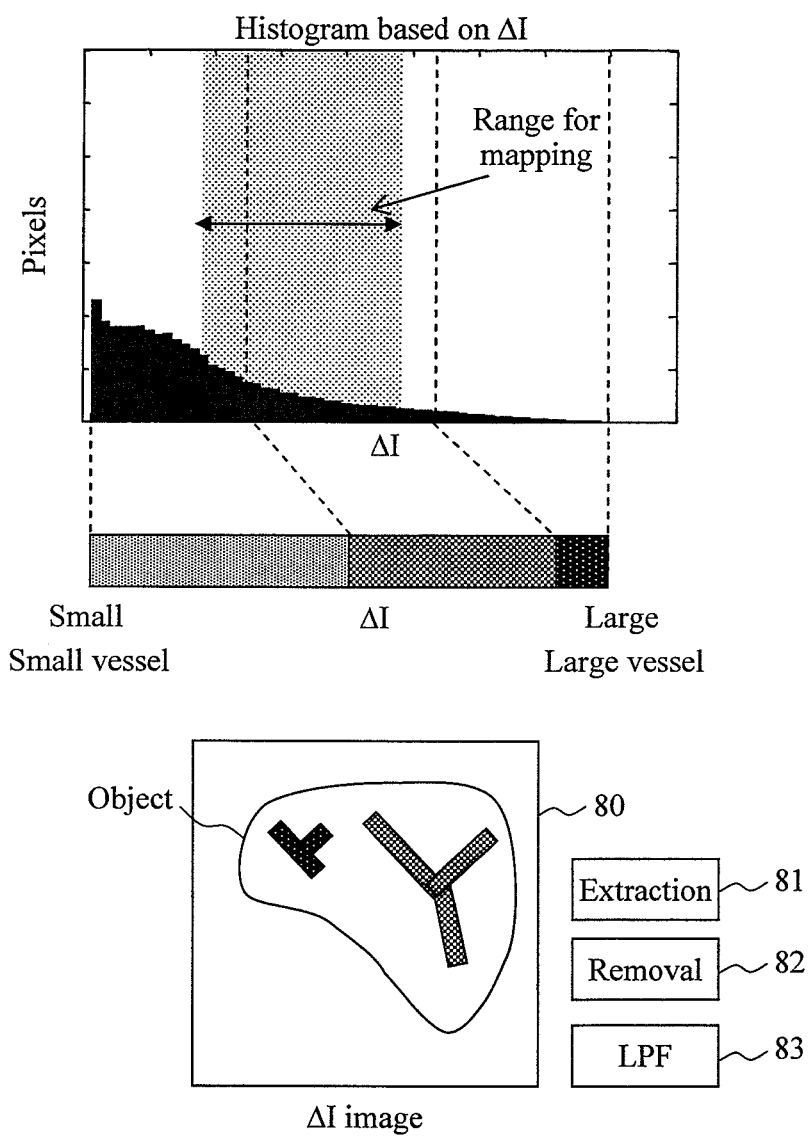
FIG. 8 describes a state where a histogram in one embodiment is reflected in a color bar of brightness.

As shown in FIG. 8, the range for mapping can be designated by dividing the histogram into three parts, for example, as in the drawing in accordance with the values of ΔI and converting the same into the range bar for displaying. The length of each section of the range bar is decided by the ratio of the number of pixels included in each divided range to the total number of pixels. In this case also, the number of pixels with ΔI=0 is not included. The axis of the range bar may directly display the magnitude of ΔI, and further description of small vessels and large vessels may be displayed for smaller ΔI and larger ΔI, respectively, for easy understanding.

Further as shown in FIG. 8, a ΔI image that is color-shaded or color-coded in accordance with the values of ΔI may be displayed together with the range bar and the histogram for ΔI, thus enabling checking pixels to be removed on the image as a result of the designation of the range for mapping for more precise adjustment.

However, the case of removing a pixel to be left or vice versa may occur. As a function to cope with this problem, as shown in FIG. 8, the ΔI image is provided with a removal button, an extraction button and a LPF (Low-Pass Filter) button. For instance, when the operator selects the extraction button and then selects a pixel or a region that the operator wants to extract always, that region can be always extracted irrespective of the range for mapping. Conversely a pixel selected by the removal button is always removed. When the operator selects the LPF button, LPF is applied to the ΔI image. Since the distribution of ΔI can be smoothed spatially, a certain collective range of pixels can be extracted and removed when the range for mapping is changed. When a pixel to be removed always is canceled, the removal button may be selected again to select the pixel, whereby the cancellation is executed. The same goes for the removal of an extracted pixel. For LPF, selecting the LPF button again will cancel the LPF.

As described above, the ultrasonic diagnostic device of the present embodiment includes: the probe 2 that transmits and receives ultrasonic signals to and from the test object 1; the receiving beamformer unit 7 that performs phasing and adding processing with respect to the ultrasonic signals received by the probe 2; the image detection unit 11 that accepts designation of information containing a starting time when a contrast agent is administered to the test object 1; the first pixel selection unit 15 that extracts, on the basis of the information on the starting time, a contrast-enhanced part with the contrast agent from image data based on the signal subjected to phasing and adding; the second pixel selection unit 17 that further extracts image data on the basis of pixel information of image data extracted by the first pixel selection unit 15; the image construction unit 16 that generates an inflow time map on the basis of image data extracted by the second pixel selection unit 17; and the display 10 that displays the inflow time map. The device has a two-stage pixel extraction function, and at the first stage, a non contrast-enhanced region is automatically removed under a loose condition, and at the second stage the operator adjusts the image based on time and brightness. Herein, as a previous step of the image adjustment based on brightness, the image may be adjusted based on time, whereby viewability of the image can be improved and the image can be easily adjusted based on time.

At the first stage of image extraction under a loose condition, noise is removed. When the condition for noise removal is too tight, even signals for a smaller vessel, for example, will be removed. Therefore, in the present invention, a loose condition as specified at Step 4 is used.

The adjustment based on brightness information (ΔI) mainly aims to remove a component other than a focused tissue. This adjustment is different from the removal processing of a non contrast-enhanced region at the first stage in that the image can be adjusted while visually observing the focused tissue and the removal effect. An important point of the processing based on ΔI resides in that the image is adjusted based on information that is not imaged. For instance, in order to remove a signal from a thick vessel and extract a thin vessel, ΔI can be set as shown in FIG. 8.

In the adjustment based on time ($t_\alpha$), the focused time range is narrowed for better image viewability, and further an increase in the number of colors for each unit time enables distinction of fine differences in blood flow dynamics with great color differences. This processing is to adjust the image based on information that is imaged, and inherently is for the focusing range and the color-coding of focused blood flow dynamics.

The above describes for Step 6 that adjustment based on brightness information follows adjustment based on time information. Actually, however, the order may be reversed, or these adjustment steps may be performed alternately. Since these adjustment steps relate to each other closely, balance between them is important for precise extraction of information on a focused vessel.

With these steps, an inflow time map is constructed and is displayed on the display 10 (Step 7).

Images displayed on the display screen 34 may include a contrast-enhanced image and an inflow time map as well as an image obtained by making the inflow time map transparent and superimposing the transparent image onto the contrast-enhanced image.

The display screen 34 is provided with a setting-change button, and selecting this button leads to display of initial settings of a time before injection of contrast agent and various parameters in the order of the processing steps of an inflow time map as shown in FIG. 9. A diagram shown in FIG. 4A about a relation between TIC and various parameters also is displayed thereon. Time before injection of contrast agent and the coefficient α of threshold brightness can be changed by directly changing corresponding numerals on the display screen. A changing result will be reflected instantly in the relation diagram of TIC. ΔI and a condition expression for pixel selection can be changed by selecting the expression and directly inputting using a keyboard attached to the ultrasonic diagnostic device. Alternatively, after selecting a parameter to be changed on the expression, the parameter may be dragged to a parameter after change, whereby the parameter can be changed. The mapping parameter is indicated with a circle on the TIC. The mapping parameter can be changed by directly inputting using a keyboard or by dragging the circle on the TIC to a new parameter to be set as the mapping parameter. Drag of the parameter may be implemented by a return button or trackball generally attached to an ultrasonic diagnostic device or a device having an alternative function therefor. When the device is equipped with a touch panel, the drag may be implemented by touching on the screen with a finger.

On the screen of setting change, ON/OFF for initial value subtraction can be further selected. In this processing, an initial value is subtracted from all values of TIC for the pixels to make the initial value of TIC 0 when various parameters are calculated by the TIC analysis unit 13. Advantages of this processing are described below. A pixel with a high brightness value at the stage before injection of contrast agent has a high $I_{max}$ value, and therefore $I_\alpha$ obtained by multiplying this by the coefficient will reduce the value of $I_{max}$ greatly. On the other hand, the processing of subtracting the initial value from TIC, the value of $I_{max}$ is reduced, and so even in the case of multiplication by the same coefficient, the degree of reduction of $I_\alpha$ with reference to $I_{max}$ becomes smaller. Therefore, ON setting of the initial value subtraction makes it easier to meet Condition 1 of the first pixel selection unit 15. This effect lies in positive extraction of pixels at a contrast-enhanced region where a tissue component mainly remains strongly. In the present embodiment, in order to selectively extract a vessel region preferentially, and since the inside of a vessel is basically drawn with low brightness on the ultrasonic image, the initial setting is set OFF.

Since various parameters are stored in the memory 14, concurrently with setting change, the image is updated. However, in the case of change of the coefficient α, since the mapping parameter $t_\alpha$ has to be calculated again based on TIC, the TIC analysis unit 13 calculates the parameter again. Alternatively, mapping parameters corresponding to specific coefficients (e.g., α=0.5, 0.6, 0.7 and 0.8) may be calculated beforehand and be stored in the memory 14, whereby recalculation by the TIC analysis unit can be avoided. When the processing range is changed, recalculation by the TIC analysis unit 13 is required in a similar manner.

The following describes a function to compare the constructed inflow time map with a past inflow time map. Since this function is useful for determination on the effect of therapy targeting at a vessel, the following describes an example of comparison between inflow time maps before and after therapy.

Figure 10:
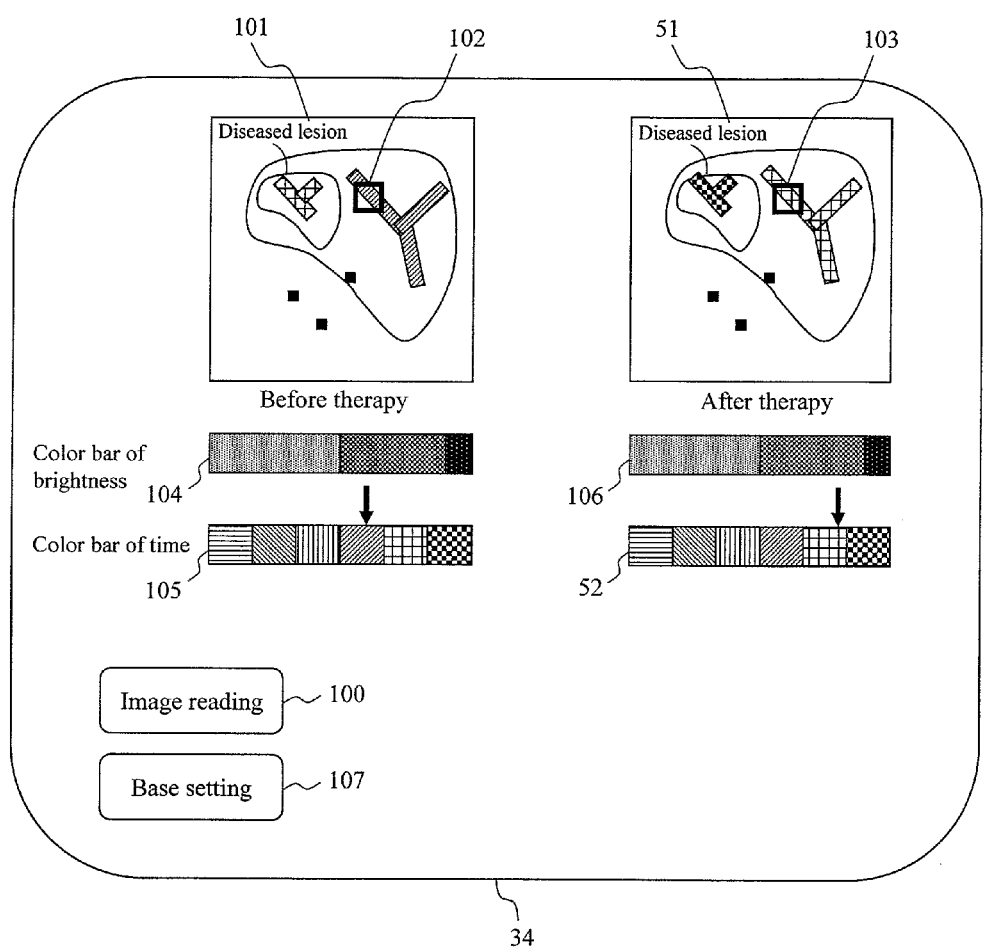
FIG. 10 describes the case of comparison between a plurality of inflow time maps in one embodiment.

Selecting an image reading 100 button provided on the display screen 34 leads to display of an inflow time map 101 in the past stored in a HDD provided in the ultrasonic diagnostic device on the display screen (FIG. 10). Assume that the inflow time map shown here describes the inflow starting time of a contrast agent, for example. Since the inflow time maps before and after therapy are differently adjusted in time range and brightness range based on ΔI, a color bar of time 105 and a range bar of brightness 104 are displayed together. In this drawing, the inflow time map 101 before therapy is an inflow time map in the past and an inflow time map after therapy is the inflow time map 51 already displayed.

Selecting a base setting 107 button displayed on the display screen 34 leads to display of base ROIs on the inflow time maps before and after therapy, the base ROIs serving as a reference of the inflow time map 101 before therapy and the inflow time map 51 after therapy (base ROI 102 before therapy and base ROI 103 after therapy). Concurrently, positions of the average time of the regions (base regions) designated by the base ROIs are indicated with arrows at the color bar of time 105 and the color bar of time 52.

Next, a ROI is set at a position of a normal vessel, for example, that is not affected by the therapy. Desirably the same vessel can be selected from the inflow time maps before and after therapy. But when such a selection is difficult, a vessel close to the focused region in position may be selected. Since the inflow starting time of each vessel can be distinguished easily based on differences in color of the inflow time map, the base ROI 102 and the base ROI 103 can be set using not only the spatial positional relation of vessels but also similarity of blood flow dynamics.

Figure 11:
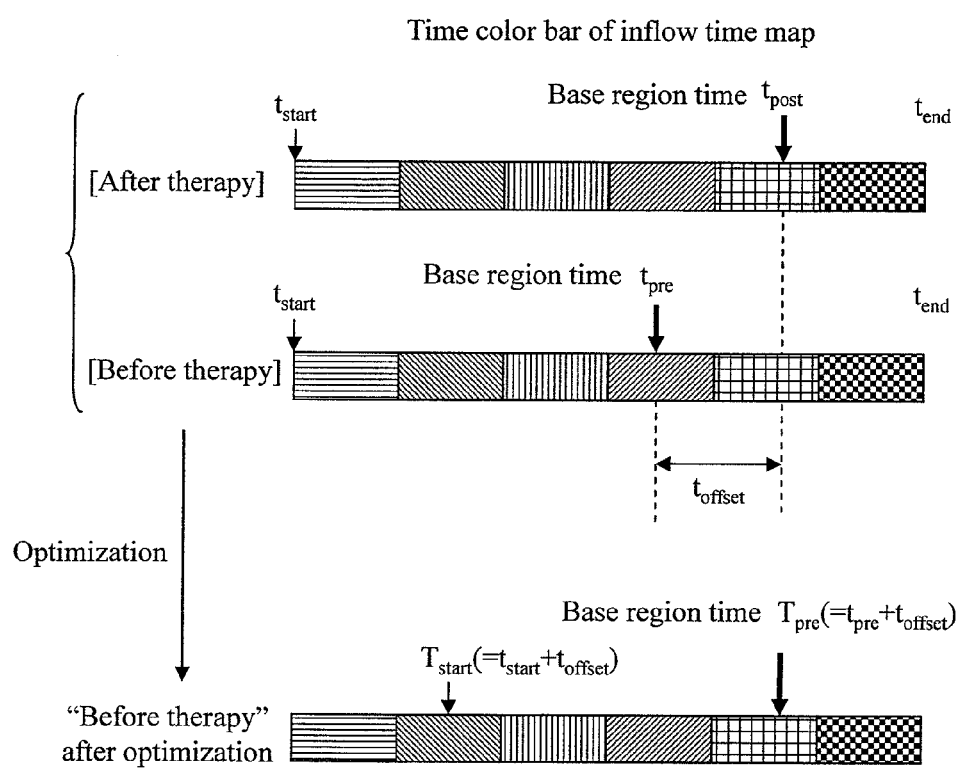
FIG. 11 describes optimization of a color bar of time in one embodiment.

Next, selecting the base setting 107 button again leads to calculation of a relative time difference ($t_{offset}$) in time range between the inflow time maps before and after therapy based on the colors of the base regions, i.e., a difference in the inflow starting time, so that a correspondence relation between the inflow time map before therapy and the color is adjusted so as to match the inflow time map after therapy. For instance, as shown in FIG. 11, when there is a time difference of $t_{offset}=t_{post}-t_{pre}$ in time at the base region between before and after therapy, $t_{offset}$ is added to the mapping parameter for all pixels of the inflow time map before therapy, so that a new mapping parameter ($T_{start}=t_{start}+t_{offset}$, $T_{pre}=t_{pre}+t_{offset}$) is reconfigured. This optimization processing makes the color-coding of the base regions, i.e., the colors of $t_{post}$ and $T_{pre}$ before and after therapy agree with each other, whereby blood flow dynamics at a lesion can be compared easily with a difference in color. A result of the color adjustment of the inflow time map before therapy is instantly reflected in the inflow time map. Accordingly, the operator can reconfigure the base region at an optimum position while checking the adjustment result on the screen. Herein, time beyond the color bar as a result of the optimization will be colorless on the inflow time map.

In a similar manner to the time range, the brightness range is optimized. The images before and after therapy may be displayed so that a contrast-enhanced image is superimposed with a semi-transparent inflow time map.

In the above description of embodiments, image data from the scan convertor 9 is used for analysis. Instead, raw data output from the receiving beamformer unit 7 may be used for analysis. Image data of the present embodiment covers not only the image data from the scan convertor 9 but also the raw data.

Figure 12:
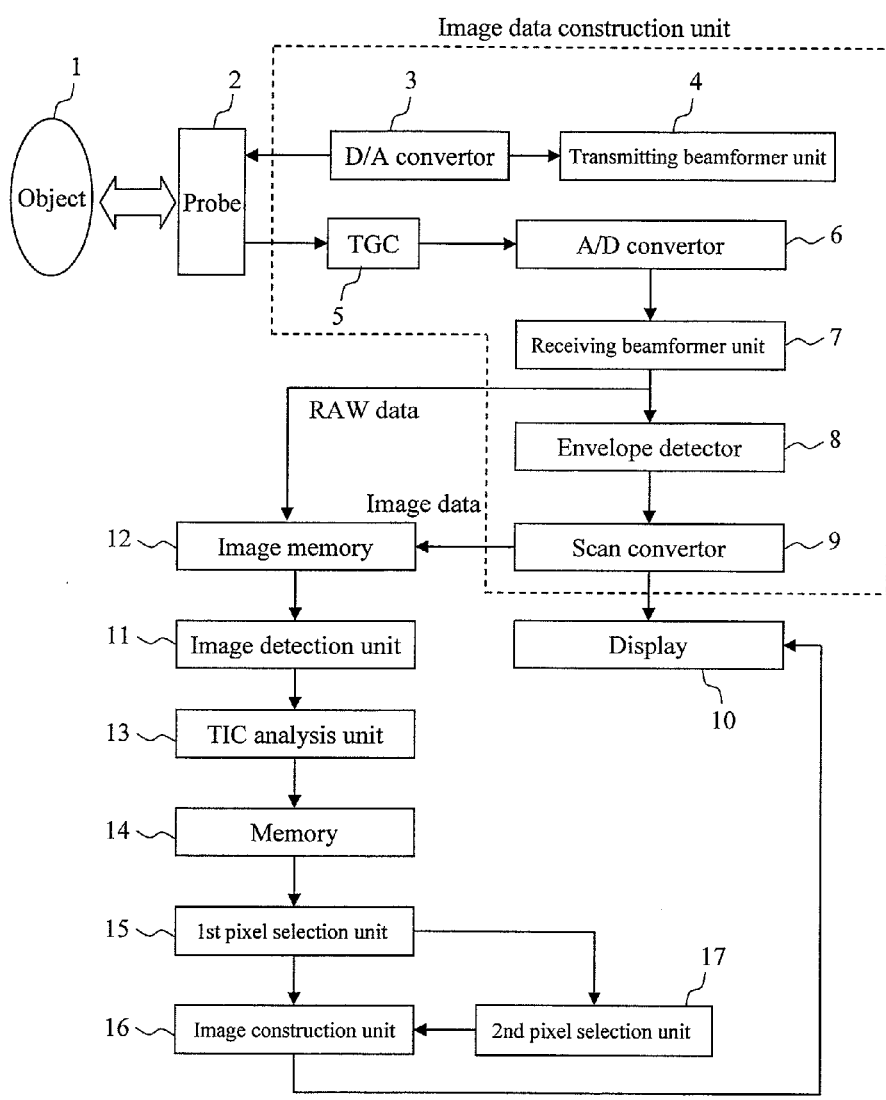
FIG. 12 is a block diagram illustrating an exemplary configuration using raw data in one embodiment.

As shown in FIG. 12, in addition to image data from the scan convertor 9, raw data from the receiving beamformer unit 7 is stored in the image memory 12. In the flowchart of FIG. 2, selection of image data (Step 1) may be implemented using the image data, and the following numerical analysis (Step 2 to Step 6) may be implemented using the raw data. The raw data directly reflects information inside the living body, and is a signal with a deeper bit-number than the image data in general. Accordingly, compared with the case of using image data, numerical analysis of higher sensitivity and higher precision is enabled, thus making a difference in mapping parameter for each part remarkable or facilitating distinction between vessels with slightly different ΔI values.

REFERENCE SIGNS LIST

1 Object
2 Probe
3 D/A convertor
4 Transmitting beamformer unit
5 TGC
6 A/D convertor
7 Receiving beamformer unit
8 Envelope detector
9 Scan convertor
10 Display
11 Image detection unit
12 Image memory
13 TIC analysis unit
14 Memory
15 First pixel selection unit
16 Image construction unit
17 Second pixel selection unit
31 Start button 32 Image data
33 Range bar of time
34 Display screen
51 Inflow time map
52 Color bar of time
53 Pixel selection button
54 Measure button
55 First ROI
56 Second ROI
80 ΔI image
81 Extraction button
82 Removal button
83 LPF button
100 Image reading button
101 Inflow time map before therapy
102 Base ROI before therapy
103 Base ROI after therapy
104 Color bar of brightness before therapy
105 Color bar of time before therapy
106 Color bar of brightness after therapy
107 Base setting button

The invention claimed is:

1. An ultrasonic diagnostic device, comprising:
a probe that transmits and receives ultrasonic signals to and from a test object;
at least one processor comprises:
a receiving beamformer unit that performs phasing and adding processing with respect to ultrasonic signals received by the probe;
an image detection unit that receives information containing a starting time when a contrast agent is administered to the test object;
a Time-Intensity Curve (TIC) analysis unit that calculates a numeric value required to construct an inflow time map for each pixel of image data, the TIC analysis unit including an analysis unit that calculates, as a difference of brightness ΔI due to the contrast agent, the difference of brightness ΔI obtained by subtracting a maximum value of brightness before injection of a contrast agent $I^{pre}_{max}$ from a threshold brightness $I_\alpha$;
a first pixel selection unit that extracts, on a basis of the information on the starting time and the calculated difference of brightness ΔI, at least one pixel in a contrast-enhanced region of the image data based on a signal subjected to phasing and adding;
an image construction unit that generates the inflow time map on a basis of the at least one pixel extracted by the first pixel selection unit;
a second pixel selection unit that further extracts at least one focused pixel from the inflow time map on a basis of the at least one pixel extracted by the first pixel selection unit, wherein the image construction unit changes the inflow time map on a basis of the at least one focused pixel extracted by the second pixel selection unit; and
a display that displays the inflow time map.

2. The ultrasonic diagnostic device according to claim 1, wherein the second pixel selection unit further extracts the at least one focused pixel on a basis of information calculated based on the starting time.

3. The ultrasonic diagnostic device according to claim 2, wherein
the second pixel selection unit extracts the at least one focused pixel on a basis of difference of brightness ΔI.

4. The ultrasonic diagnostic device according to claim 3, wherein the image construction unit generates a color bar of time where colors vary with a change in time from the starting time and an inflow time map, and wherein the image construction unit colors each extracted pixel with colors specified by the color bar.

5. The ultrasonic diagnostic device according to claim 4, wherein the second pixel selection unit can change the starting time $t_{start}$ and an ending time $t_{end}$ of a processing period ($t_{start}$-$t_{end}$), and wherein the colors in the color bar change based on the changed $t_{start}$ and $t_{end}$.

6. The ultrasonic diagnostic device according to claim 4, wherein
the image construction unit generates the color bar of time so as to allow an operator to designate a starting point ($t_{start}$) and a ending point ($t_{end}$) of a processing period ($t_{start}$-$t_{end}$) by interacting with the display, whereby parameters of pixels beyond the processing period are made 0 and the colors of the color bar are changed having an upper limit and a lower limit corresponding to the starting point ($t_{start}$) and the ending point ($t_{end}$), respectively, and the setting is instantly reflected in the inflow time map.

7. The ultrasonic diagnostic device according to claim 4, wherein
the image construction unit generates a color bar of brightness where color changes with magnitude of brightness corresponding to a histogram representing a relation between the difference of brightness ΔI and pixels of the image data,
in the color bar of brightness, the color bar of brightness is divided into a number of divided sections, and a width of each divided section is adjusted in accordance with the number of divided sections and a total number of pixels in each divided section, and
the display displays the color bar of brightness and information on a thickness or a type of a vessel, and magnitude of ΔI, and
the second pixel selection unit extracts the at least one focused pixel on a basis of a color of each at least one focused pixel corresponding to a color on the color bar of brightness.

8. The ultrasonic diagnostic device according to claim 3, wherein
the second pixel selection unit and the image construction unit operate to display a histogram representing a relation between the difference of brightness ΔI and the at least one pixel extracted by the first pixel selection unit, wherein the second pixel selection unit accepts a range of ΔI for mapping to be displayed on the histogram, changes parameters of pixels beyond the accepted range, and changes the at least one focused pixel extracted by the second pixel extraction unit to thereby change in the inflow time map.

9. The ultrasonic diagnostic device according to claim 3, wherein the display screen allows an operator to change a starting point ($t_{start}$) and a predetermined time ($t_{pre}$) corresponding to a predetermined time range ($t_{pre}$-$t_{start}$) used by the image detection unit, a parameter calculated by the TIC analysis unit and a conditional expression, and wherein the first pixel selection unit extracts the at least one pixel in accordance with the conditional expression.

10. The ultrasonic diagnostic device according to claim 1, wherein the image construction unit further generates a first numeric value of a mapping parameter at a region designated by a first region of interest (ROI) on the display and a second numeric value of a mapping parameter at a region designated by a second ROI on the display, wherein the second numeric value is one of an absolute value or a relative value with reference to the first numeric value.

11. The ultrasonic diagnostic device according to claim 1, wherein at least one of the first pixel selection unit or the second pixel selection unit extracts from image data at a predetermined time range ($t_{pre}$-$t_{start}$) ahead of the processing time range ($t_{start}$-$t_{end}$), where $t_{start}$ is a starting time, $t_{end}$ is an ending time, and $t_{pre}$ is a predetermined time delay.

12. The ultrasonic diagnostic device according to claim 1, wherein the display displays the inflow time map and a past inflow time map constructed in the past while displaying base regions of interest (ROIs) on the inflow time map and the past inflow time map to be compared so as to quantitatively compare a relation between colors and time for each base ROI, and the ultrasonic diagnostic device further includes a scan converter configured to perform an interpolation function of making a mapping parameter and color-coding of each of the base ROIs agree with each other.

13. The ultrasonic diagnostic device according to claim 1, wherein the image data includes raw data output from the receiving beamformer unit.

14. An ultrasonic image display method, comprising the steps of:
- transmitting and receiving ultrasonic signals between a test object and an ultrasonic probe;
- performing, by a receiving beamformer unit, phasing and adding processing with respect to ultrasonic signals received by the ultrasonic probe;
- receiving, by an image detection unit, information containing a starting time when a contrast agent is administered to the test object;
- calculating, by a Time-Intensity Curve (TIC) analysis unit, a numeric value required to construct an inflow time map for each pixel of image data, the TIC analysis unit including an analysis unit that calculates, as a difference of brightness $\Delta I$ due to the contrast agent, the difference of brightness $\Delta I$ obtained by subtracting a maximum value of brightness before injection of a contrast agent $I^{pre}_{max}$ from a threshold brightness $I_\alpha$;
- extracting, by a first pixel selection unit, on a basis of the information on the starting time and the calculated difference of brightness $\Delta I$, a contrast-enhanced region of the image data based on a signal subjected to phasing and adding;
- generating, by an image construction unit, the inflow time map on a basis of the at least one pixel extracted by the first pixel selection unit
- further extracting, by a second pixel selection unit, at least one focused pixel from the inflow time map on a basis of the at least one pixel extracted by the first pixel selection unit;
- changing, by the image construction unit, the inflow time map on a basis of the at least one focused pixel extracted by the second pixel selection unit; and
- displaying, by a display, the inflow time map,
- wherein at least one processor comprises the receiving beamformer unit, the image detection unit, the Time-Intensity Curve (TIC) analysis unit, the first pixel selection unit, the image construction unit, and the second pixel selection unit.

* * * * *